United States Patent [19]
Peters et al.

[11] Patent Number: 5,910,109
[45] Date of Patent: Jun. 8, 1999

[54] NON-INVASIVE GLUCOSE MEASURING DEVICE AND METHOD FOR MEASURING BLOOD GLUCOSE

[75] Inventors: Richard K. Peters; Donald Elmerick, both of Tallmadge, Ohio

[73] Assignee: Emerging Technology Systems, LLC, Akron, Ohio

[21] Appl. No.: 08/803,066

[22] Filed: Feb. 20, 1997

[51] Int. Cl.⁶ ........................................................ A61B 5/00
[52] U.S. Cl. ................................................................ 600/316
[58] Field of Search .................................... 600/316, 309, 600/310, 322

[56] References Cited

U.S. PATENT DOCUMENTS

| | | |
|---|---|---|
| 4,882,492 | 11/1989 | Schlager . |
| 4,901,728 | 2/1990 | Hutchinson . |
| 5,009,230 | 4/1991 | Hutchinson et al. . |
| 5,028,787 | 7/1991 | Rosenthal et al. . |
| 5,063,531 | 11/1991 | Kawai et al. . |
| 5,070,874 | 12/1991 | Barnes et al. . |
| 5,086,229 | 2/1992 | Rosenthal et al. . |
| 5,183,042 | 2/1993 | Harjunmaa et al. . |
| 5,204,532 | 4/1993 | Rosenthal . |
| 5,222,495 | 6/1993 | Clarke et al. . |
| 5,243,983 | 9/1993 | Tarr et al. . |
| 5,267,152 | 11/1993 | Yang et al. . |
| 5,313,941 | 5/1994 | Braig et al. . |
| 5,360,004 | 11/1994 | Purdy et al. . |
| 5,361,758 | 11/1994 | Hall et al. . |
| 5,379,764 | 1/1995 | Barnes et al. . |
| 5,383,452 | 1/1995 | Buchert . |
| 5,398,681 | 3/1995 | Kupershmidt . |
| 5,433,197 | 7/1995 | Stark . |
| 5,448,992 | 9/1995 | Kupershmidt . |
| 5,460,177 | 10/1995 | Purdy et al. . |
| 5,515,847 | 5/1996 | Braig et al. . |
| 5,529,755 | 6/1996 | Higashio et al. . |
| 5,533,509 | 7/1996 | Koashi et al. . |
| 5,551,422 | 9/1996 | Simonsen et al. . |
| 5,579,232 | 11/1996 | Tong et al. . |

FOREIGN PATENT DOCUMENTS 3541 165 A1 5/1987 Germany .

OTHER PUBLICATIONS

Subcommittee on Oversight and Investigations. U.S. House of Representatives Commitee on Commerce. Sep. 26, 1996. Re: Consumer Access to Home Testing Services and Devices.

Diabetes Interview—The Newspaper for the Diabetes Commmunity, Issue No. 50, Sep. 1996.

PR News Wire Article, Nov. 26, 1996.

*Primary Examiner*—Scott M. Getzow
*Attorney, Agent, or Firm*—Calfee, Halter & Griswold

[57] ABSTRACT

A glucose measuring device for determining the concentration of glucose in intravascular blood within a body part of a subject. The device includes light sources having a wavelength of 650, 880, 940 or 1300 nm to illuminate the fluid. Receptors associated with the light sources for receiving light and generating a transmission signal representing the light transmitted are also provided. A support piece is including for supporting the light sources associated with their respective light sources. The support piece is adapted to engage a body part of a subject. Finally, a signal analyzer, which includes a trained neural network, determines the glucose concentration in the blood of the subject. A method for determining the glucose concentration is also provided which calibrates a measuring device and sets the operating current for illuminating the light sources during operation of the device. Once a transmission signal is generated by receptors receiving light via the light sources and illuminated blood, and the high and low values from each of the signals are stored in the device, and averaged to obtain a single transmission value for each of the light sources. The averaged values are then analyzed to determine the glucose concentration, which value is displayed on the device.

15 Claims, 5 Drawing Sheets

NON-INVASIVE GLUCOSE MEASURING DEVICE AND METHOD FOR MEASURING BLOOD GLUCOSE

TECHNICAL FIELD

The present invention relates generally to a medical diagnostic measurement instrument, and, more specifically, to a device and method for obtaining non-invasive quantitative measurements of blood glucose in patients.

BACKGROUND

The frequent monitoring of blood glucose levels in individuals with diabetes mellitus has become a major factor in the care of such patients over the past decade. Currently, it is possible for the diabetes patient and health care professionals to measure and record blood glucose levels using a variety of portable devices. Due to the need for multiple daily measurements, invasive blood for samples are a burden on the patient and often expensive. As a result, non-invasive devices using spectroscopic techniques, and which are battery powered and use solid-state electronics, have begun to be commercialized. Used at home, these devices allow diabetes patients to monitor and respond to fluctuations in blood glucose on a daily basis.

One example of such a device is disclosed in U.S. Pat. No. 5,070,874 to Barnes, et al. ("the U.S. Pat. No. '874"). As set forth in the U.S. Pat. No. '874, human blood glucose concentration levels vary greatly, and are found within the range of 0–600 milligrams per deciliter (mg/dl). Normal human blood glucose levels are in the approximate range of 80–110 mg/dl. Devices of the type disclosed in the U.S. Pat. No. '874 involve measurement of blood components using near infrared radiation and spectroscopic absorption techniques. Additional devices of this type are disclosed in U.S. Pat. Nos. 5,379,764 and 4,882,492, as well as numerous others, which make use of both reflectance and transmission spectroscopic analysis techniques.

Problems with these prior art devices have resulted due to several issues. One problem is the overlap of the spectrum of glucose with other blood sugars and chemicals. Another relates to hemoglobin-glucose binding, which renders discrete spectral measurements difficult. Also, spectroscopic techniques are typically unable to discriminate between sugars that are metabolized and those that are excreted, resulting in erroneous readings. Still further, prior art devices have failed to address issues which directly impact the accuracy of the measurements taken, such as the spectral effect produced by the skin and tissue, as well as variable blood vessel and skin thickness and composition.

As a result of these and other problems, the repeatability and resulting accuracy of such devices has not been in the range it is desired. The U.S. Food and Drug Administration is currently advising that non-invasive glucose measuring devices should have an accuracy in the range of 15% error or less.

SUMMARY OF THE INVENTION

According to the present invention, a transmission glucose measuring device is provided which uses a signal sensor assembly to illuminate intravascular blood or fluid components in the body. The assembly includes near infrared light sources on one external surface of a translucent body to illuminate blood or fluid, and light receptors positioned on an opposite external surface of the same body, to receive respective signals representing the radiation transmittance through the tissue and blood or fluid components illuminated. Preferably, four (4) light sources emit near infrared and infrared light between 650 and 1300 nm wavelengths. A fifth (5) possible light source may also be used, which would repeat one of the previous four (4) wavelengths. The light sources in the preferred embodiment are light emitting diodes (LEDs) which are pulsed at 1 kiloHertz (kHz) for a 1 millisecond (ms) pulse width. Each receptor, or sensor, operates at a time when the other receptors are off to avoid further noise and signal contamination. The pairs of LEDs and opposite receptors are mounted on a spring biased support for convenient attachment of the LEDs and receptors to the body part. In the preferred embodiment, the spring biased support is for mounting on external surfaces of the human ear. It is understood that numerous shapes and configurations for the support could be used, depending on the shape of the body or body part to be measured.

Prior to use of the device, upon turning the device on a self-check is performed to ensure that all LEDs and respective receptors are operating to specification. When the device is to be used on a new subject, the device is first calibrated for the skin or tissue and blood flow characteristics of the subject. Such calibration is believed to enable improved accuracy and predictability in glucose measurement in the present device, since factors such as tissue thickness and composition, as well as blood flow, are taken into consideration. Intensity calibration involves setting the intensity of the LEDs based on an LED intensity factor which is derived from the high and low data values measured from a pulse waveform signal.

The pulse of the subject is measured using one of the LEDs and its associated receptor as a pulse monitor. The high and low blood flow data values collected by the pulse monitor to obtain the pulse waveform signal of the subject are also converted and stored in a digital processor, such as an LED signal processor. Once the high and low pulse waveform signal values are known, the blood flow characteristics of the subject are used for the intensity calibration.

The intensity factor is established based upon initial readings of the pulse waveform signal. Current is increasingly supplied to the LED to increase the intensity of the light source in a stepped fashion at one of multiple increments, until a minimally distorted desirable signal is received by the receptor. Once an acceptable signal is received, this selected level of LED intensity is stored by the processor, and becomes the level of current applied to each of the remaining LEDs during operation of the device. Additionally, each of the LEDs is operated to determine that it is properly operational and that its respective receptor is receiving the LED's signal at the desired LED intensity. The LEDs are continuously checked by the device to ensure proper operation. In the event no signal is received, the device prevents a measurement from being taken and issues a warning notice to the operator.

Still another step in device calibration involves determining from the pulse waveform signal when measurements or readings should be taken by the device. Measurements of the LED signal are preferably only taken at a midpoint in the blood flow cycle, or at the "baseline" of the pulse waveform signal. For example, the difference between the high and low data values from the pulse waveform signal result in a value which is provided to the signal processor for establishing the timing of measurements, or signal generation, taken by the device with respect to the blood flow of the subject.

The device then initiates the operation and measurement of each of the LED signals, preferably through an ear lobe of the subject. Measurements from each of the LEDs are preferably taken several predetermined times at each of the high and low pulsatile values measured over 5 milliseconds, with the resulting sensor signal values amplified in a sample and hold amplifier in the LED signal processor, converted in an analog-to-digital (A/D) converter, and averaged together to obtain a single digital data value for each of the LED signals.

The pre-processed digital signal from the LED signal processor is then provided to a further digital processor, preferably via a personal computer interface of the type well known to those of skill in the art. The digital processor is preferably a personal computer supporting a trained neural network containing predetermined or target spectral glucose transmittance and absorbance data over a range of 0 to 600 mg/dl, for determining the glucose level of the subject from the digital signal provided. The glucose level is then provided to a digital display for review by the subject.

Other features and advantages the present device will become apparent from the following detailed description of the preferred embodiment made with reference to the accompanying drawings, which form a part of the specification.

BRIEF DESCRIPTION OF DRAWINGS

In the accompanying drawings, which are incorporated in and constitute a part of this specification, embodiments of the device described are illustrated, and together with the general description above, and the detailed description below, exemplify the device of the present invention.

DETAILED DESCRIPTION OF THE PREFERRED EMBODIMENT

Figure 1:
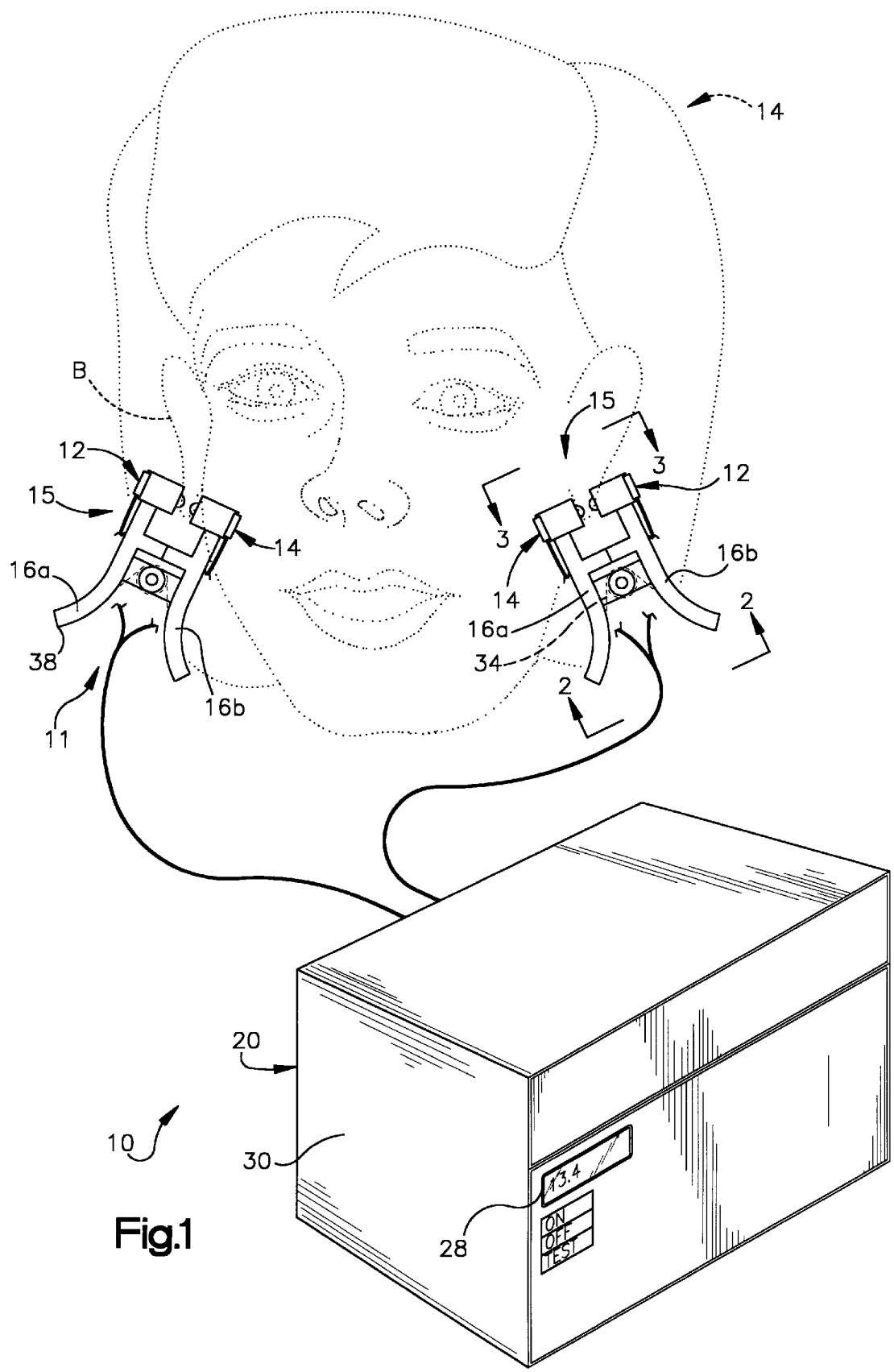
FIG. 1 is a schematic illustration of a transmission glucose measuring device as disclosed.
Figure 5:
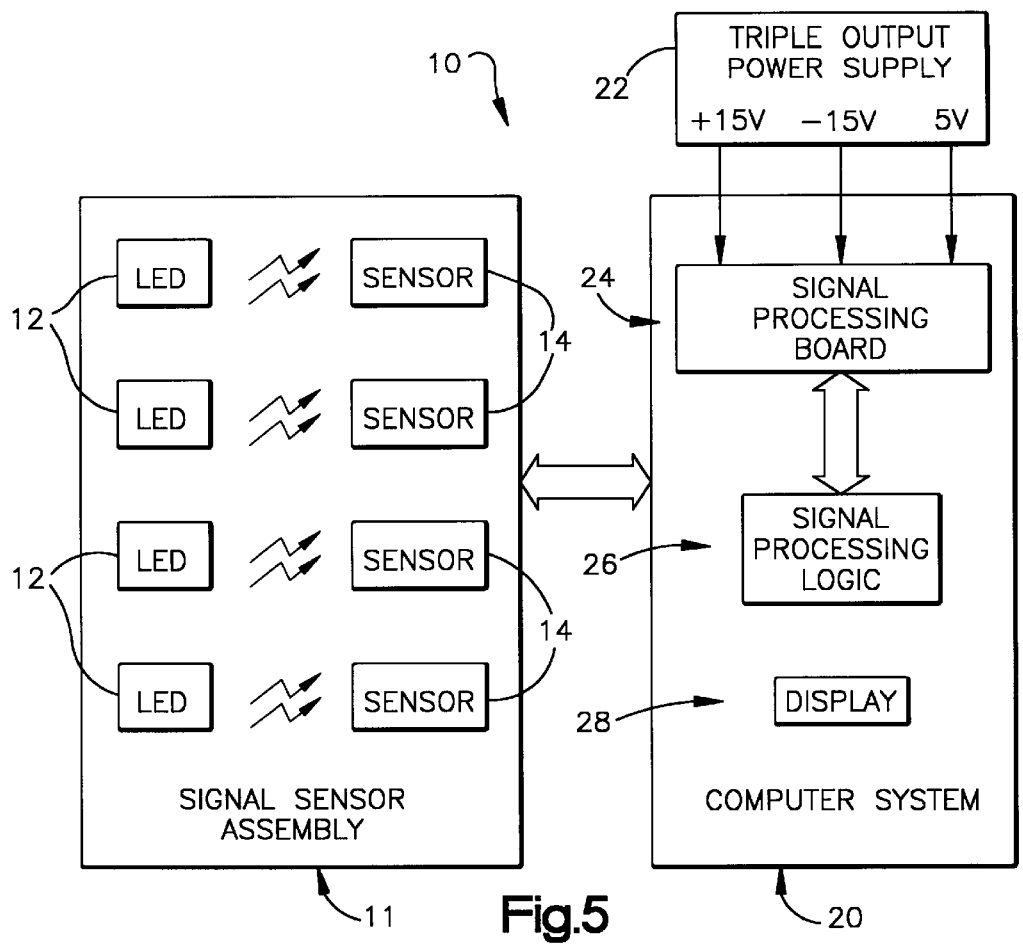
FIG. 5 is a high level block diagram of the present device showing a signal sensor assembly, triple output power supply and computer system.

FIG. 1 is a schematic illustration of the non-invasive transmission glucose measuring device 10 disclosed. The device includes a signal sensor assembly 11 comprising light sources or LEDs 12 and associated receptors 14 mounted on an assembly housing 15 comprising opposing spring biased support pieces 16. In the preferred embodiment, each support piece 16 has one or more LED 12 and associated receptors 14, for attachment to a body part B of a subject H. The device additionally includes a computer system 20 and a power supply 22 as shown in FIG. 5. The computer system 20 comprises a signal processing board 24, signal processing logic 26 and a display 28. The computer system components are housed within a black box or housing 30. The housing has dimensions of approximately 4 inches by 8 inches. The display 28 provides the glucose concentration measured and calculated by the present device for viewing by the user.

In the preferred embodiment, the signal sensor assembly 11 and its components, as shown in FIGS. 1 to 4, includes the support pieces 16 which are adapted for spring biased engagement surrounding portions of the human ear B. It is understood that other body parts such as the nose, fingers or toes could also be used. The support piece 16a supports and is interconnected with the light sources 12, such that the LED is positioned to illuminate the surface of the ear as illustrated. The support piece 16b supports and is interconnected with the receptors 14 associated with each LED, and are positioned opposite from their respective LEDs for receiving light transmitted from the LED through the ear B.

In the preferred embodiment, 4 or 5 LEDs emitting near infrared and infrared light at wavelengths of 650, 880, 940 and 1300 nm, with a fifth possible light source used to repeat one of the previous four wavelengths. The LEDs light sources in the preferred embodiment are pulsed at 1 kilo-Hertz (kHz) for a 1 millisecond (ms) pulse width. The LEDs include a housing portion 12a and a bulb portion 12b. The LEDs are available from Optoelectronics of Sunnyvale, Calif. The conventional receptors 14 generating the transmission signals through the body part also include a housing portion 14a and a sensor portion 14b. The receptors are also available from Optoelectronics. Each combination of LED and receptor operate at a time when the others pair or pairs are off to avoid further noise and signal contamination. The LED housing 12a and bulb portion 12b is more fully shown in FIG. 4. It should be understood that the receptor housing 14a and bulb portion 14b, is identical in its support structure, such that no further discussion is required. Specifically, the support pieces 16a, 16b include an additional support body 80 for receiving the LED or receptor housing portions 12a, 16a. The support body 80 may be manufactured of any rigid polymer material, such as Delrin®. The support body 80 includes an opening 82 for receiving the LED or receptor housing portion 12a, 14a. At the end of the housing portions 12a, 14a, a floating support plate 84 is provided which is engaged with the bulb portion 12b, 14b and is movable with respect to the housing portion 12a, 14a. Additionally, an end fitting 86 is provided which is in press fit engagement with the support body opening 82, and includes a bulb opening 87 for receiving the bulb portion 12b, 14b, of the LEDs and receptors. Intermediate the end fitting 86 and the floating support plate 84, compression springs 88 are provided. In this arrangement, the bulb portion 12a, 14a of the LEDs and receptors are movable with respect to the support body 80, such that the bulb portions are in light spring biased or in floating engagement with the body B once they are in communication with the subject H.

Figure 2:
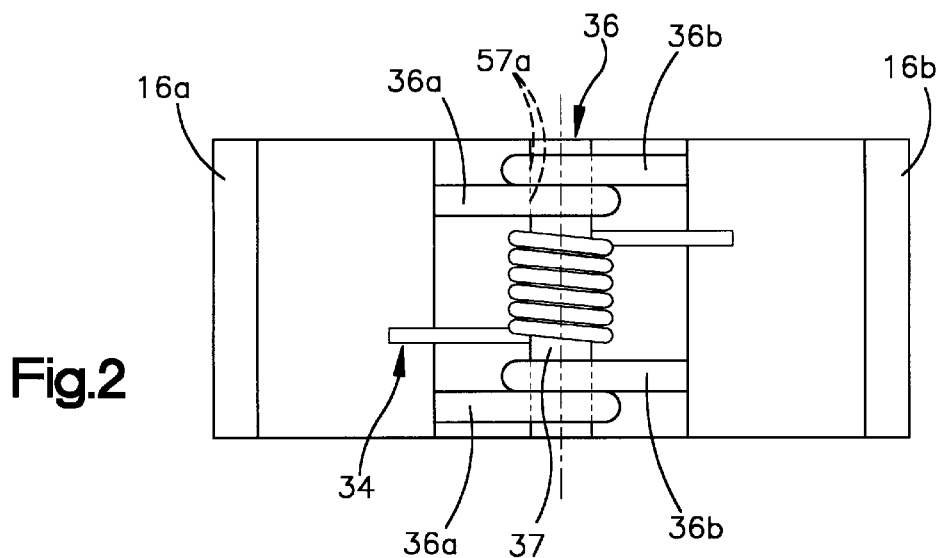
FIG. 2 is a schematic rear end view of a signal sensor assembly, or the support pieces for supporting the light sources and receptors, taken along the line 2—2 in FIG. 1.
Figure 3:
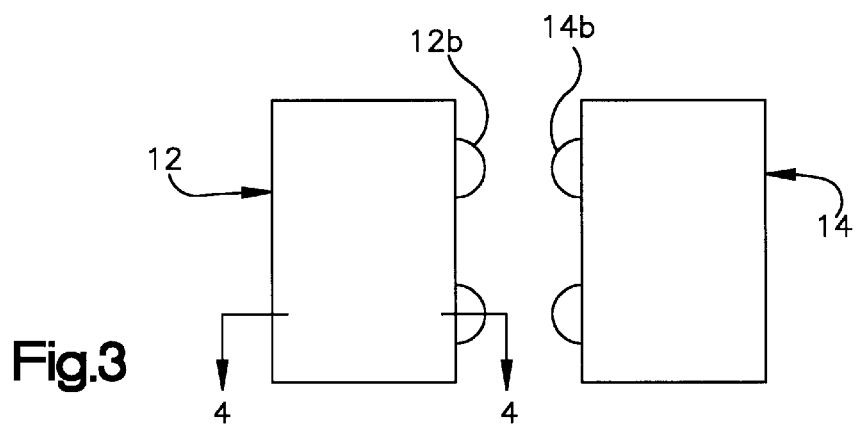
FIG. 3 is a schematic front end view of the support pieces for supporting the light sources and receptors taken along the line 3—3 in FIG. 1.
Figure 4:
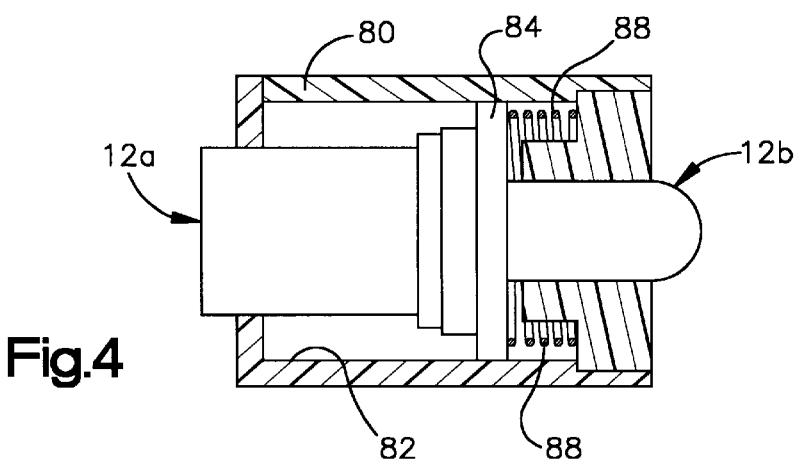
FIG. 4 is a schematic cut-away view of the support piece for supporting the light sources and associated receptors taken along the line 4—4 of FIG. 3.

As shown in FIGS. 1 and 2, the support pieces 16a, 16b, or first and second plates which comprise the support piece 16, are interconnected at a pivot point 36 positioned intermediate the support pieces, and include a torsion spring 34 for biasing the support pieces toward one another. Legs 36a, 36b are interconnected with the support pieces 16a, and 16b, respectively, and are engaged through an opening 37a in the legs by an axle 37 for pivoting motion about the pivot point 36. Thus, the support pieces 16a, 16b, are manually moved toward one another on first ends 38 spaced from the end of the support pieces with the LEDs and receptors 12, 14, to provide a space between the LEDs and receptors for the ear, as shown in FIG. 1. Once the assembly 11 is positioned with one of each of the support pieces 16a, 16b on either side of the body part, the first ends 38 are gradually released to engage the LEDs and receptors with the body part. It is particularly noted that the spring 34 must have a sufficient force to compressingly engage both the LEDs and the receptors with the ear B, but that the spring force is not so great that the intravascular blood flow within the ear is impacted.

As described here and shown in the preferred embodiment, the signal sensor assembly 11 operates in a manner similar to a spring biased clothes pin for securing clothing to a clothes line. It is important to note that the force of spring 34 and the arrangement of the support pieces 16a, 16b, must be such that the LEDs and receptors are at all times during operation of the device, positioned opposite from one another to enable proper illumination and receipt of the light transmission through the body part B. Thus, it is contemplated that one may choose to use an alternate arrangement of the spring biased support pieces, for example, changing the spring 34 position to eliminate the pivot 36, and to alternatively provide parallel movement of the each of the support pieces, with the axis of the spring transverse to the support pieces.

As shown schematically in FIG. 5, the signal sensor assembly 11 is electrically interconnected with the computer system 20 to drive illumination of the LEDs 12 and to receive signals from the receptors 14 corresponding to the light transmitted through the ear for further processing and display. The FIG. 5 high level block diagram of the present device shows the signal sensor assembly, triple output power supply and computer system. The triple output power supply 22 includes +15 volt, −15 volt and a +5 volt power supply outputs.

Figure 6:
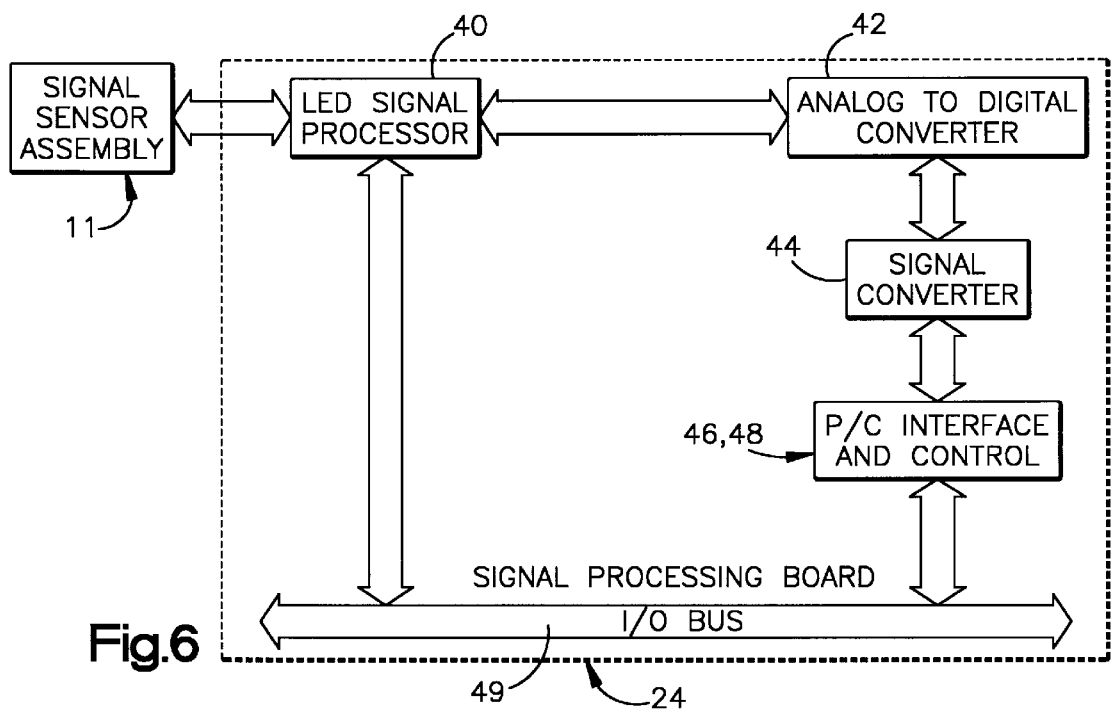
FIG. 6 is a high level block diagram illustrating the major components of a signal processing board of the present device.

As illustrated in FIG. 6 the major components of the signal processing board 24 include a LED signal processor 40, an analog-to-digital converter 42, a signal converter 44, a P/C interface 46 and a control circuit 48. Data is transferred between the signal processing board 24 and the P/C interface via an I/O bus 49. The P/C interface 46 of the preferred embodiment is a KB-8 PC-IN-A-Box from KILA of Boulder, Colo., or a 1×6×3 Compac, Inc. device. It should be understood that numerous conventionally available devices may be used. The illustrated conventional components are in circuit communication with each other as shown in FIG. 6. It should be noted in connection with the conventional A-to-D converter that additional known techniques are also used to enhance the signal to noise ratio such as the heterodyne detection scheme. This detection technique is well known to those of skill in the art and eliminates the DC offset problems caused by background illumination. Also, the use of coherent gating are used to improve the overall measurement accuracy since the measurement of interest is performed during a period of maximum blood flow. This technique enables the dwell time between the blood pulses to be used to obtain a measurement that yields a DC background value which can be subtracted from the peak value. This technique also eliminates measurement problems associated with tissue hydration, non-uniform tissue thickness and density, as well as patient to patient variation.

Figure 7:
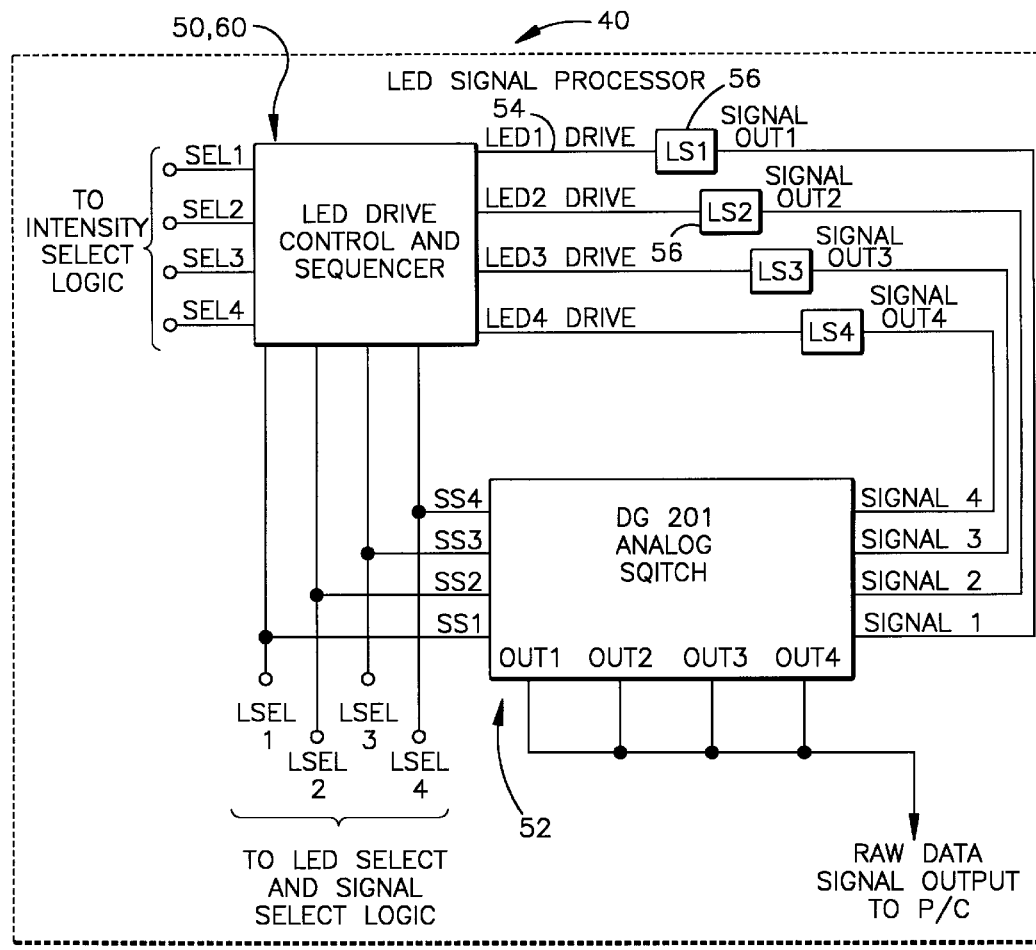
FIG. 7 is a block diagram of a LED signal processor of the present device.

Referring now to FIG. 7, a block diagram of the LED signal processor 40 of the present device is shown. The LED signal processor 40 includes a LED drive circuit 60 and sequencer circuit 50, an analog switch 52 and a plurality of connections 54 to a plurality of LED/sensor blocks 56 which are referenced as LS1, LS2, LS3 and LS4. The conventional components are in circuit communication with each other as shown in FIG. 7.

Figure 8:
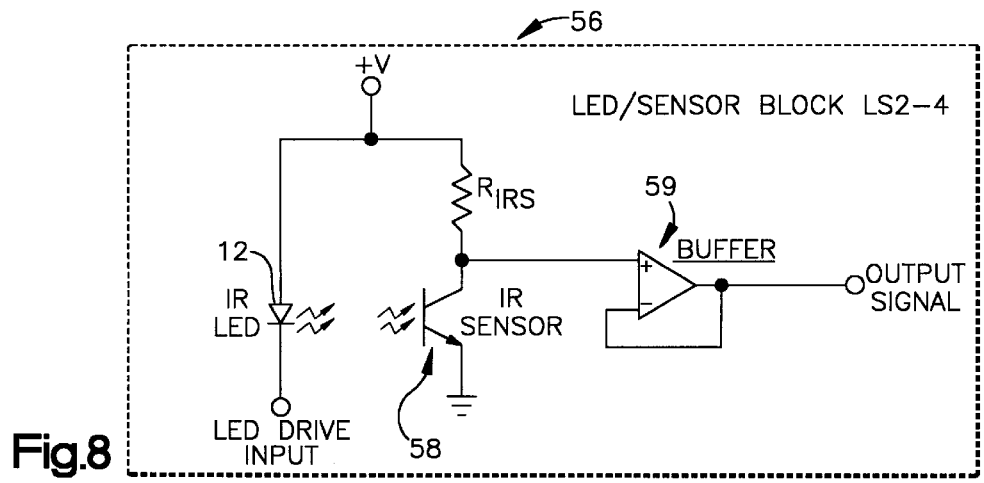
FIG. 8 is a schematic diagram of LED/sensor blocks LS1–LS4 of the present device.

Referring now to FIG. 8, a schematic diagram of LED/sensor blocks 56 or LS1–LS4 of the present device are illustrated. Each LED/sensor block 56 includes a LED 12, a sensor 58 and a buffer 59. These well known components are in circuit communication with each other as shown.

Figure 9:
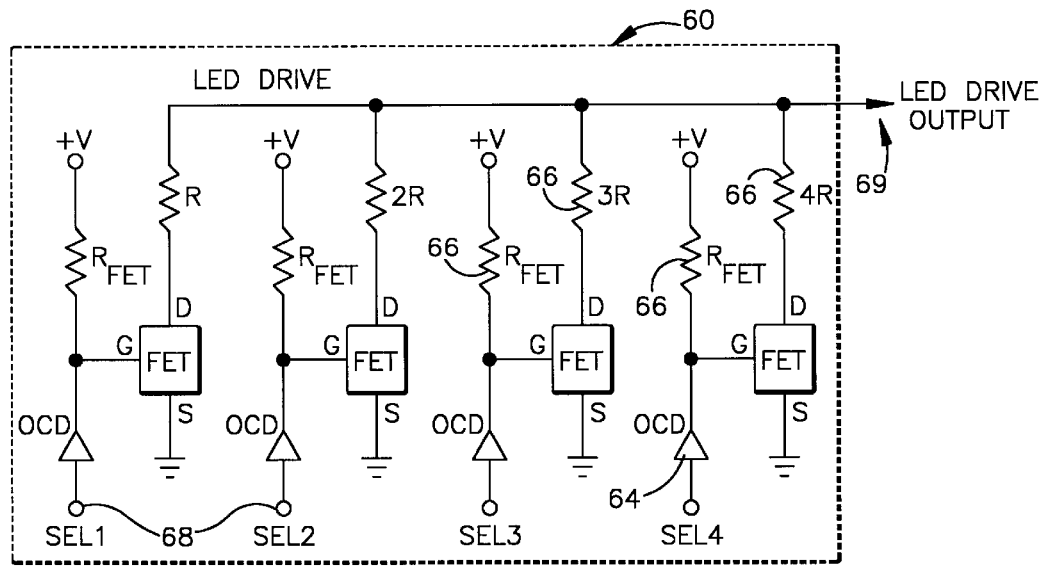
FIG. 9 is a schematic diagram of an LED drive circuit of the present device.

Illustrated in FIG. 9 is a schematic diagram of the LED drive circuit 60 of the present device. The LED drive circuit 60 includes a plurality of transistors (e.g. FET's) 62, drivers (e.g. OCD) 64 and a plurality of resistors (R, 2R, 4R, 8R and $R_{FET}$) 66. The LED drive circuit 60 also includes inputs SEL1 through SEL4 68 and an output 69. The conventional circuit elements are in circuit communication with each other as shown.

Figure 10:
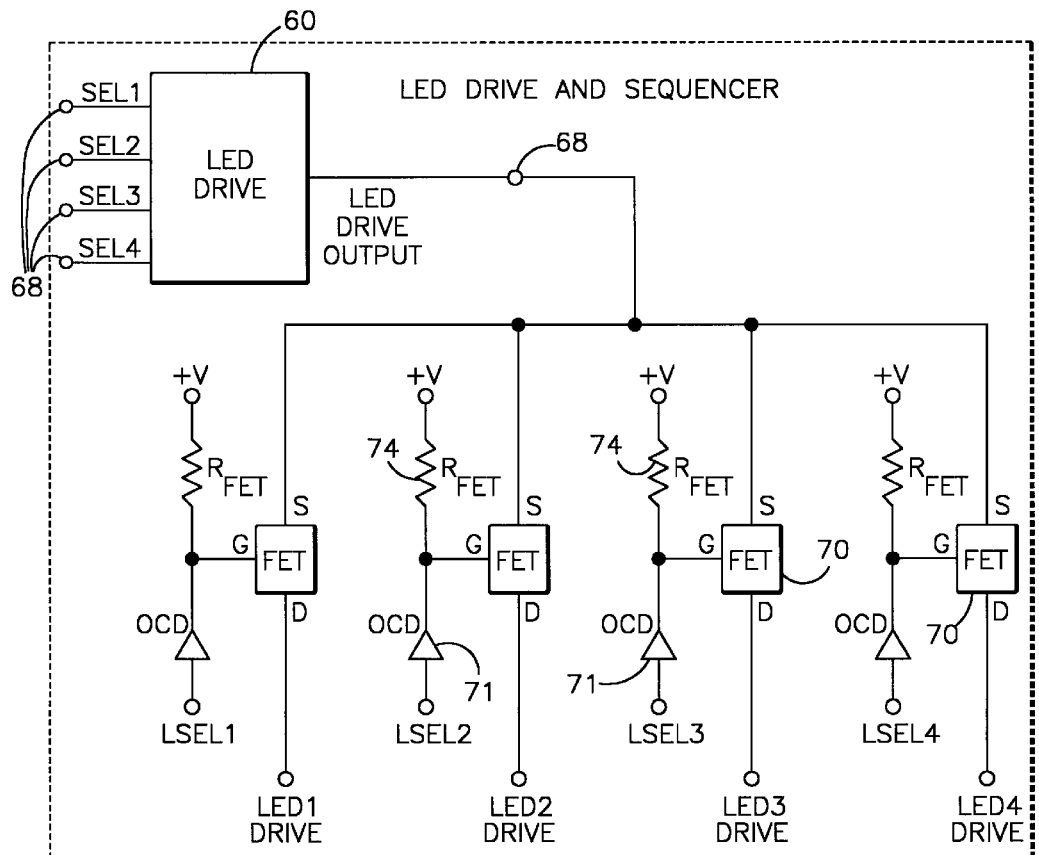
FIG. 10 is a block/schematic diagram of a LED drive and sequencer circuit of the present device.

Illustrated in FIG. 10 is a block/schematic diagram of the LED drive 60 and sequencer circuit 50 of the present invention. The LED drive and sequencer includes the LED drive circuit 60 of FIG. 5, and a plurality of transistors (e.g. FET's) 70, drivers (e.g. OCD) 71, and a plurality of resistors (R, 2R, 4R, 8R and $R_{FET}$) 74. The LED drive 60 and sequencer circuit 50 also includes inputs LSEL1 through LSEL4, SEL1 through SEL4, and outputs LED1 DRIVE through LED4 DRIVE. The conventional circuit elements are in circuit communication with each other as shown.

The P/C interface 46 of the signal processing logic 26 incorporates a conventional trained neural network 27, forming part of the signal processing logic which determines the measured glucose concentration based on a comparison of the measured and pre-processed transmission signal with pre-determined spectral data stored in the neural network 27. Once calculated, the glucose concentration is provided to the display 28 mounted in the black box 30.

The conventional trained neural network 27, which is a standard back propagation network with a single hidden layer, allows the device to learn and discriminate between the target glucose substance from other blood components. In order to obtain the ideal or target glucose values over the spectral range of 700 to 1800 nm, tests were conducted on glucose dissolved in simulated blood. The simulated blood was a solution of 14.5% bovine hemoglobin and 5% albumin with synthetic noise in distilled water. These are the typical concentrations of hemoglobin and albumin found in human blood. The ideal spectra values were measured using a VIS/NIR spectrometer. The measured spectra were of simulated blood containing glucose concentrations in the range of 50 mg/dl to 600 mg/dl. Also, an empty curette data set was taken for reference, as sell as one albumin data set, one deionized water data set and seven hemoglobin data sets. An ideal measurement was taken without noise considerations, and a noisy measurement was taken which included a 5% noise component. During training the network adjusts its internal coefficients or weights until the network can predict the target value associated with each input to within a predetermined acceptable tolerance. The preferred neural network would contain approximately 30–40 sets of transmittance data corresponding to 30–40 different glucose levels. Set forth in Table 1 are the descriptions of the test substances

TABLE 1

| Description | Concentration | N.N. Target | Training Output | Training Error | Test Output | Test Error |
| --- | --- | --- | --- | --- | --- | --- |
| Glucose | 9% | 0.4 | 0.40191 | 0.5% | 0.4018 | 0.4% |
| Glucose | 18% | 0.5 | 0.49055 | 1.9% | 0.4882 | 2.4% |
| Glucose | 36% | 0.6 | 0.60116 | 0.2% | 0.6014 | 0.2% |
| Albumin | | 0.3 | 0.29828 | 0.6% | 0.2939 | 2.0% |
| Deionized Water | | 0.2 | 0.20058 | 0.3% | 0.2005 | 0.2% |
| Hemoglobin | | 0.7 | 0.69965 | 0.0% | 0.6939 | 0.9% |
| Hemoglobin | | 0.72 | 0.71972 | 0.0% | 0.7159 | 0.6% |
| Hemoglobin | | 0.8 | 0.80149 | 0.2% | 0.7870 | 1.6% |
| Hemoglobin | | 0.82 | 0.81838 | 0.2% | 0.8112 | 1.1% |
| Hemoglobin | | 0.84 | 0.83949 | 0.1% | 0.8357 | 0.5% |
| Hemoglobin | | 0.86 | 0.86286 | 0.3% | 0.8526 | 0.9% |
| Hemoglobin | | 0.88 | 0.87260 | 0.8% | 0.8596 | 2.3% |
| Empty | | 0.1 | 0.09956 | 0.4% | 0.1004 | 0.4% |

The device is generally operated as follows. First, a self-check of the device is performed to confirm operation of the signal sensor assembly 11, including the LEDs 12 and associated receptors 14. Next, when the device is used on a new subject, several calibration steps are performed to initialize the device. One such step is setting the intensity of the LEDs 12. This is determined based on the LED intensity factor. The LED intensity factor is measured based on from the high and low data values measured from the pulse waveform signal taken from the pulse of the subject. The pulse of the subject is taken on one of the LEDs 12 and its associated receptor 14. The high and low pulse data values are collected and used to obtain the pulse waveform signal which is converted from analog to digital and stored in the computer system 20 within the LED signal processor 40.

The intensity factor is established using the pulse waveform signal. During initialization of the device, current is increasingly and incrementally supplied to an LED 12 to increase the intensity of the light source. This stepped process is performed until a minimally distorted predetermined desirable signal is received by the associated receptor 14. Once an acceptable signal is received, the then operating level of LED intensity is stored by the LED signal processor 40, and becomes the current applied to each of the remaining LEDs 12 during regular operation of the device. Through continuous checking of the LEDs and receptors, proper operation of the device is maintained at all times. A warning notice is provided to the operator in the event improper operation is detected.

Next in the calibration process, the device calculates when measurements or readings should be taken by the device. Measurements of the LED signals are preferably only taken at a midpoint in the subject's blood flow cycle. This has been previously described as the "baseline" of the pulse waveform signal, which, in the present device, means the difference between the high and low data values from the pulse waveform signal. As these signals are stored within the LED/sensor blocks 58 within the signal processor 40, timing of the operation of the LEDs 12 is readily determined using the drive circuit 60 as indicated in FIGS. 7–10.

Once these initial operations are completed, the signal sensor assembly 11 is then operated at the times and increments calculated by the computer system 20, in particular the LED drive 60 and sequencer circuit 50, to measure each of the LED signals, all as indicated in FIGS. 7–10. Measurements from each of the LEDs are taken several predetermined times at each of the high and low pulsatile values measured over 5 milliseconds, with the resulting sensor signal values amplified as described, where in the LED signal processor 40, the values are converted in the analog-to-digital converter 42, and averaged together to obtain a single digital data value for each of the LED signals. The pre-processed digital signal from the LED signal processor 40 is then provided to the signal processing logic 26 within the P/C interface 46 of the computer system 20 via the I/O bus 49 as illustrated in FIG. 6. The trained neural network 27 supported on the P/C interface compares the glucose transmittance data provided via the LED signal processor 40 with the predetermined or target spectral glucose transmittance data stored within the neural network, and upon finding a comparative value determines the glucose level of the subject from the digital signal provided. The glucose level selected by the neural network is then provided to the digital display 28. In the event additional operations of the device on the same subject are desired, the subject merely manually selects the "test" button provided on the housing 30 to run another test. The device then repeats the entire process previously described, including initialization, since the support pieces may have been moved, or some other problem may have occurred.

The preferred form of the glucose measuring apparatus 10 has been described above. However, with the present disclosure in mind it is believed that obvious alterations to the preferred embodiment, to achieve comparable features and advantages in other assemblies, will become apparent to those of ordinary skill in the art.

We claim:

1. A glucose measuring device for determining the concentration of glucose in fluid within a body part of a subject, comprising:

a) a first light source emitting near infrared or infrared light having a wavelength of between 650 and 1300 nm to illuminate the fluid, a second light source emitting near infrared or infrared light having a second wavelength of between 650 and 1300 nm to illuminate the fluid which is different from the wavelength of said first light source, and at least one receptor associated with said light sources for receiving light emitted by said light sources and transmitted through the fluid and body part of the subject and generating transmission signals representing the light transmitted from said first and second light sources;

b) a support piece having a first plate for supporting said light sources, and a second plate movable with respect to said first plate for supporting said receptor associated with said light sources;

c) said support piece adapted to place a body part of a subject intermediate said first and second plates and to alternately illuminate the body part and fluid using one of said light sources; and d) a signal analyzer interconnected with said receptor for receiving said transmission signals and for determining from the transmission signals the glucose concentration in the fluid within the illuminated body part.

2. The device of claim 1, wherein said second light source has a wavelength of approximately 940 nm.

3. The device of claim 2, further including a third light source emitting near infrared or infrared light having a third wavelength of either 650, 880, 940 or 1300 nm, which is different from the wavelengths of said light source and second light source, to illuminate the fluid, and a third receptor associated with said third light source for receiving light emitted by said third light source and transmitted through the fluid and a body part of the subject and generating a third transmission signal representing the light transmitted from said third light source.

4. The device of claim 3, wherein said third light source has a wavelength of approximately 650 nm.

5. The device of claim 3, wherein said fourth light source has a wavelength of approximately 1300 nm.

6. The device of claim 2, further including a fourth light source emitting near infrared or infrared light having a third wavelength of either 650, 880, 940 or 1300 nm, which is different from the wavelengths of said light source, second and third light sources, to illuminate the fluid, and a fourth receptor associated with said fourth light source for receiving light emitted by said fourth light source and transmitted through the fluid and a body part of the subject and generating a fourth transmission signal representing the light transmitted from said fourth light source.

7. The device of claim 6, further including a second support piece having a first plate for supporting said third and fourth light sources, a second plate movable with respect to said first plate for supporting said third and fourth receptors associated with their respective third and fourth light sources, and said second support piece adapted to place a body part of a subject intermediate said first and second plates of said second support piece and to alternately illuminate the body part and fluid using said third and fourth sources.

8. The device of claim 7, wherein said first and second plates of said support piece are spring biased to provide contacting engagement of said light source supported on said first plate with one side of the body part, and contacting engagement of said receptor supported on said second plate with an opposite side of the body part.

9. The device of claim 1, further providing a display monitor interconnected with said signal analyzer for displaying the glucose concentration determined.

10. The device of claim 9, wherein said signal analyzer is a trained back propagation neural network with a single hidden layer.

11. The device of claim 10, wherein the fluid measured within the body part is intravascular blood and the body part is the ear.

12. A method for determining the glucose concentration in intravascular blood within a body part of a subject comprising the steps of:

i) calibrating a non-invasive glucose measuring device by:
   a) measuring the pulse waveform of the subject using one of a first or second light source;
   b) incrementally increasing an electrical current powering one of said first or second light sources, incrementally reading a transmission signal generated in a first or second receptor, and comparing said incremental transmission signals until a predetermined desired quality of transmission signal is received from said first or second light source;
   c) establishing said electrical current which resulted in the desired quality of transmission signal as the operating current for powering said first and second light sources during operation of said glucose measuring device;

ii) operating said non-invasive glucose measuring device by:
   a) illuminating intravascular blood within a body part using first or second light sources positioned adjacent to and engaging the body part for multiple consecutive readings, said light sources having different wavelengths of between 650 and 1300 nm and being powered at the established electrical current;
   b) generating a transmission signal in first or second receptors from each of said first or second light sources via the illuminated intravascular blood of the body part, said first or second receptors positioned adjacent to and engaging the body part on an opposite side of the body part from the first and second light sources, respectively;
   c) storing high and low values from each of the multiple transmission signals from each of the light sources;
   d) averaging each of the multiple sets of high and low values from each transmission signal generated to obtain a single transmission value for each of said light sources;
   e) analyzing the averaged transmission signal values to determine the glucose concentration in the intravascular blood within the body part; and
   f) displaying the glucose concentration.

13. The method of claim 12, wherein the step of illuminating intravascular blood within a body part using first or second light sources positioned adjacent to and engaging the body part for multiple consecutive readings is timed to coincide with a midpoint of high and low values of the pulse waveform of the subject.

14. The method of claim 13, wherein the step of illuminating intravascular blood within a body part using first and second light sources is performed alternately, such that only one light source is illuminated at any one time.

15. The method of claim 14, wherein the step of analyzing the averaged transmission signal values comprises submitting the values to a back propagation neural network with a single hidden layer which is trained with glucose spectral data.

* * * * *